(12) United States Patent
Isaacs et al.

(10) Patent No.: US 8,435,288 B2
(45) Date of Patent: May 7, 2013

(54) SYSTEM AND METHOD FOR STORING, SHIPPING AND INJECTING OCULAR DEVICES

(75) Inventors: Thomas L. Isaacs, Oldsmar, FL (US); Hayden Beatty, Dunedin, FL (US); William B. Wright, Antioch, TN (US)

(73) Assignee: Lenstec Barbados Inc., Christ Church (BB)

(*) Notice: Subject to any disclaimer, the term of this patent is extended or adjusted under 35 U.S.C. 154(b) by 528 days.

(21) Appl. No.: 11/525,360

(22) Filed: Sep. 22, 2006

(65) Prior Publication Data

US 2008/0077237 A1    Mar. 27, 2008

(51) Int. Cl.
    *A61F 2/16* (2006.01)
(52) U.S. Cl.
    USPC .......................................................... 623/6.12
(58) Field of Classification Search .................. 623/6.12; 606/107
    See application file for complete search history.

(56) References Cited

U.S. PATENT DOCUMENTS

| | | | |
|---|---|---|---|
| 4,715,373 A * | 12/1987 | Mazzocco et al. | 606/107 |
| 4,763,650 A | 8/1988 | Hauser | |
| 4,834,094 A * | 5/1989 | Patton et al. | 606/107 |
| 4,862,885 A * | 9/1989 | Cumming | 606/107 |
| 5,304,182 A * | 4/1994 | Rheinish et al. | 606/107 |
| 5,410,576 A * | 4/1995 | Perrotti | 376/272 |
| 5,578,042 A | 11/1996 | Cumming | |
| 5,902,278 A | 5/1999 | Aguilar | |
| 5,947,975 A | 9/1999 | Kikuchi et al. | |
| 6,174,315 B1 | 1/2001 | Chambers et al. | |
| 6,406,481 B2 | 6/2002 | Feingold et al. | |
| 6,491,697 B1 | 12/2002 | Clark et al. | |
| 6,503,275 B1 * | 1/2003 | Cumming | 623/6.12 |
| 6,506,195 B2 | 1/2003 | Chambers et al. | |
| 6,537,283 B2 | 3/2003 | Van Noy | |
| 6,605,093 B1 * | 8/2003 | Blake | 606/107 |
| 6,607,537 B1 | 8/2003 | Binder | |

(Continued)

FOREIGN PATENT DOCUMENTS

| | | |
|---|---|---|
| EP | 0711571 | 5/1996 |
| JP | 10309293 | 11/1998 |
| WO | WO0103611 | 1/2001 |
| WO | WO 2007098622 | 9/2007 |

OTHER PUBLICATIONS

IXEF polyarylamide; Solvay Advanced Polymers; Design and Molding Guide; Version 2.1; pp. 1 through 75.

(Continued)

*Primary Examiner* — Ryan Severson
*Assistant Examiner* — Rachel S Papeika
(74) *Attorney, Agent, or Firm* — John J. Love; Claude E. Cooke, Jr.; Cooke Law Firm (57) ABSTRACT

A shipping system for a medical device, such as implantable lens for an eye, is provided that may be reconfigured from a shipping mode into an injection mode without manually handling the contained lens or other device. Upon manufacture, a lens may be placed within the system assembly in the shipping configuration. While in the shipping configuration, the lens is kept in its desired shape and within a selected environment. Upon arrival at the destination, the user may attach fittings for injection of the device into a body. The process of changing from the shipping to the injection mode deforms the device into a shape suitable for injection.

17 Claims, 11 Drawing Sheets

U.S. PATENT DOCUMENTS

| | | |
|---|---|---|
| 6,921,405 B2 | 7/2005 | Feingold et al. |
| 6,976,989 B1 * | 12/2005 | Vincent .......................... 606/107 |
| 7,320,690 B2 | 1/2008 | Beavers et al. |
| RE40,185 E | 3/2008 | Kikuchi et al. |
| 2001/0041897 A1 | 11/2001 | Feingold et al. |
| 2005/0222579 A1 | 10/2005 | Vaquero et al. |
| 2007/0000801 A1 | 1/2007 | Mauran et al. |
| 2008/0077237 A1 | 3/2008 | Isaacs et al. |

OTHER PUBLICATIONS

Notification of Reasons of Refusal; Aug. 28, 2012; pp. 1-2; Hiroe & Associates, patent professional corporation.

* cited by examiner

SYSTEM AND METHOD FOR STORING, SHIPPING AND INJECTING OCULAR DEVICES

BACKGROUND OF THE INVENTION

1. Field of the Invention

This invention relates to medical apparatus. More specifically, this invention relates to a container for a foldable device, such as an intraocular lens, that enables a physician to inject the device directly into an eye without removing the device from the shipping container.

2. Description of Related Art

Figure 1:
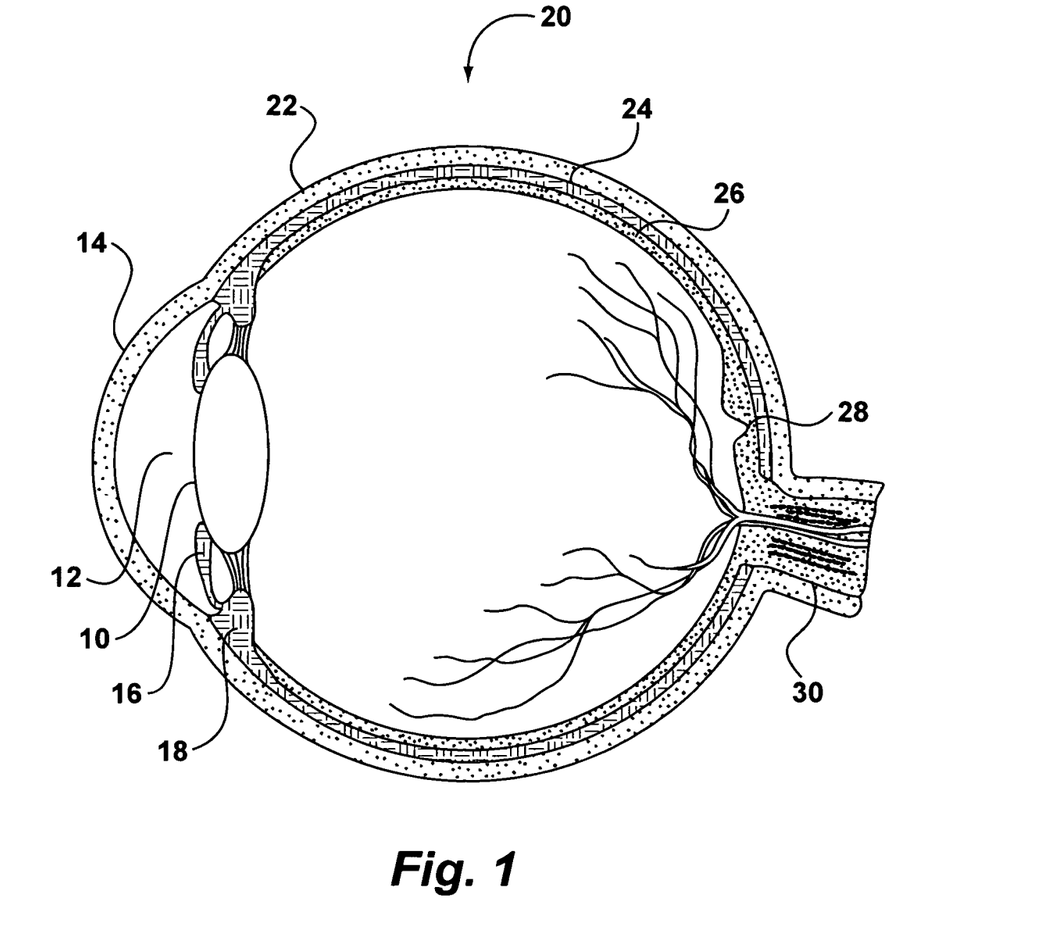
FIG. 1 is an illustration of an eye.

FIG. 1 shows the basic structure of an eye. Eye 20 has natural lens 10, which is partially exposed at pupil 12 underneath cornea 14. Around pupil 12 is iris 16. Lens 10 is attached to ciliary body 18 within sclera 22. Other tissue, such as choroid 24, retina 26 and fovea 28 are also present. Finally, optic nerve 30 carries optical signals from eye 20 to the brain.

For various reasons, such as cataract or injury, the natural lens of an eye may need replacement. Synthetic lenses for replacement are available from various manufacturers, who make the lens to the required optical characteristics. Intraocular lenses are made from three types of materials: silicone, hydrophobic (normally made of an acrylic) and hydrophilic. Silicone and acrylic lenses are shipped dry, whereas hydrophilic lenses are shipped in a wet condition. The index of refraction of the materials increases in the order: silicone, hydrophobic (acrylic) and hydrophilic. Hydrophilic lenses exhibit better biological compatibility and produce less inflammation after insertion into a patient's eye. While hydrophilic lenses are more beneficial, the cost and wet-storage requirements mean that, in many situations, lenses with a lower refractive index (but dry-shipped) are used instead of hydrophilic lenses. One of the advantages of dry-shipped lenses is that the lens can be shipped pre-loaded for injection.

Hydrophilic lenses are shipped in a sterile solution to preserve sterility and physical characteristics. Upon arrival at the medical facility, the lens is removed from its shipping container and placed in a device that is used to inject the lens into an eye. Unfortunately, the lens must be handled manually to transfer it from the shipping container to the injection device. The transfer from shipping container to the injection device introduces the potential for contamination of the lens. Moreover, the transfer procedure is often tedious and time-consuming. There is, therefore, a need in the art to eliminate problems associated with moving a lens from its shipping container to an injection device, thereby enabling greater use of hydrophilic intraocular lenses and other implantable devices.

SUMMARY OF INVENTION

The present invention is a shipping and storage container for a medical implant, such as a lens for an eye. The present invention is constructed and arranged so that it is quickly and efficiently reconfigured from a shipping mode into an injection device without manually handling the implant itself. Upon manufacture, the medical implant is placed within the present invention in its shipping configuration. While in the shipping configuration, the medical implant can be kept in its desired (undistorted) shape within a suitable fluid and protected by the body of the container. Upon arrival at the medical facility, a physician may attach one or more injection related fittings to the container (e.g., a syringe plunger and injection needle). The technician or physician may then operate the device to transition the container from the shipping configuration to the injection configuration. The injection configuration of the present invention forms the medical implant into a shape suitable for injection. The present invention thus obviates the need for a technician or physician to handle the medical implant directly before injection into the patient, thereby precluding a potential source of contamination and reducing the time necessary to perform the medical procedure. The present invention is generally applicable for medical devices that are folded before insertion into a patient.

The present invention may be susceptible to various modifications and alternative forms. Specific embodiments of the present invention are shown by way of example in the drawings and are described herein in detail. It should be understood, however, that the description set forth herein of specific embodiments is not intended to limit the present invention to the particular forms disclosed. Rather, all modifications, alternatives, and equivalents falling within the spirit and scope of the invention as defined by the appended claims are intended to be covered.

BRIEF DESCRIPTION OF DRAWINGS

Referring now to the drawings, the details of the preferred embodiments of the present invention are illustrated.

DETAILED DESCRIPTION

Referring now to the drawings, the details of exemplary embodiments of the present invention are schematically illustrated. Like elements in the drawings will be represented by like numbers.

Figure 2A:
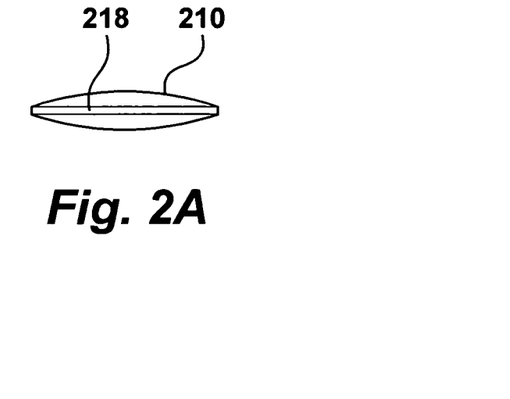
FIG. 2A is an end elevation view of one form of an intraocular lens.
Figure 2B:
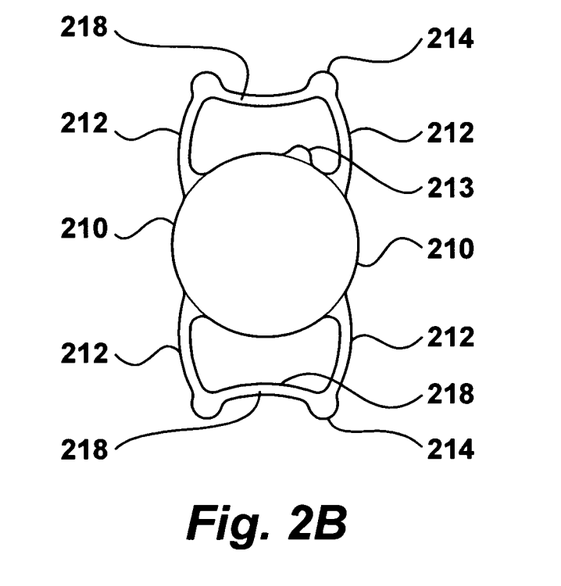
FIG. 2B is a plan view of the intraocular lens of FIG. 2A.

Referring to FIG. 2A, a front elevation view of an intraocular lens with optic 210 and haptic 218 is illustrated. A plan view of the lens and haptics is shown in FIG. 2B. The lens may have side plates 212, orientation tab 213 and foot plates 214.

Figure 3A:
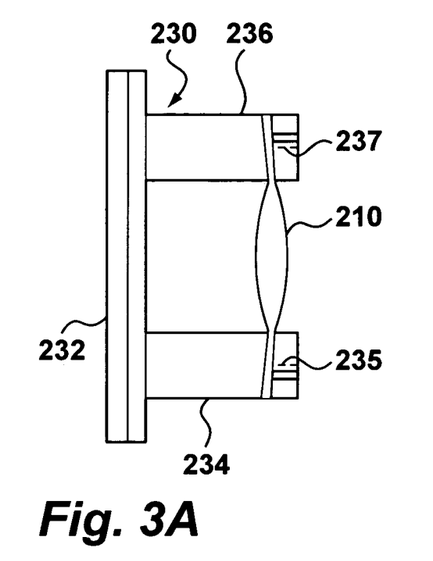
FIG. 3A is a side elevation view of an intraocular lens holder of one embodiment of the present invention.
Figure 3B:
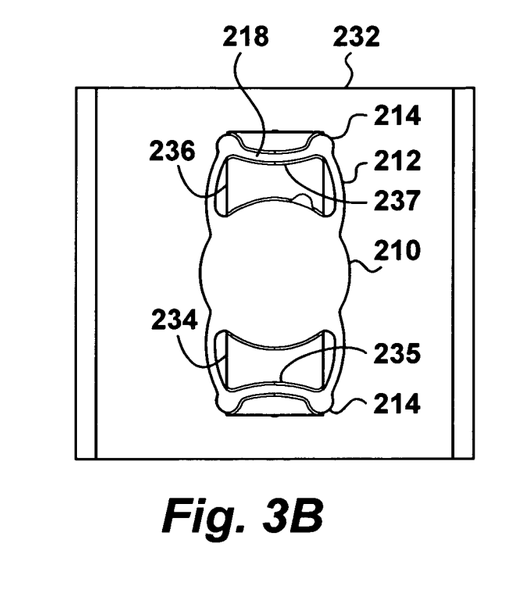
FIG. 3B is a plan view of the intraocular lens holder of FIG. 3A.
Figure 3C:
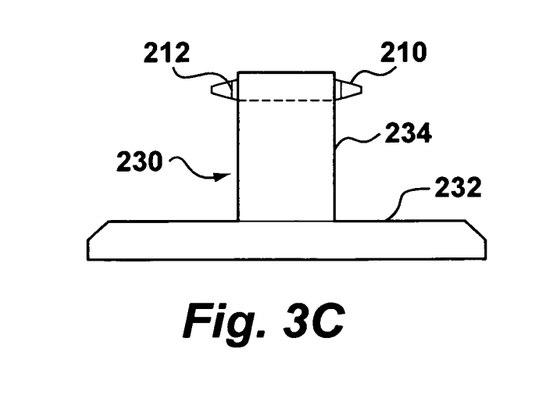
FIG. 3C is a front elevation view of the intraocular lens holder of FIG. 3A.

FIG. 3A shows optic 210 with its haptics fitted onto lens holder 230. Lens holder 230 has base 232 and legs 234 and 236. The legs have channels 235 and 237, respectively, within which lens haptics 218 are placed to secure the lens for shipping, as illustrated in FIG. 3B. FIG. 3C shows a front elevation view of optic 210 as it sits within the legs of lens holder 230. Lens holder 230 may be adapted for any lens or other device that is to be folded and inserted through an opening or incision into a patient.

Figure 4A:
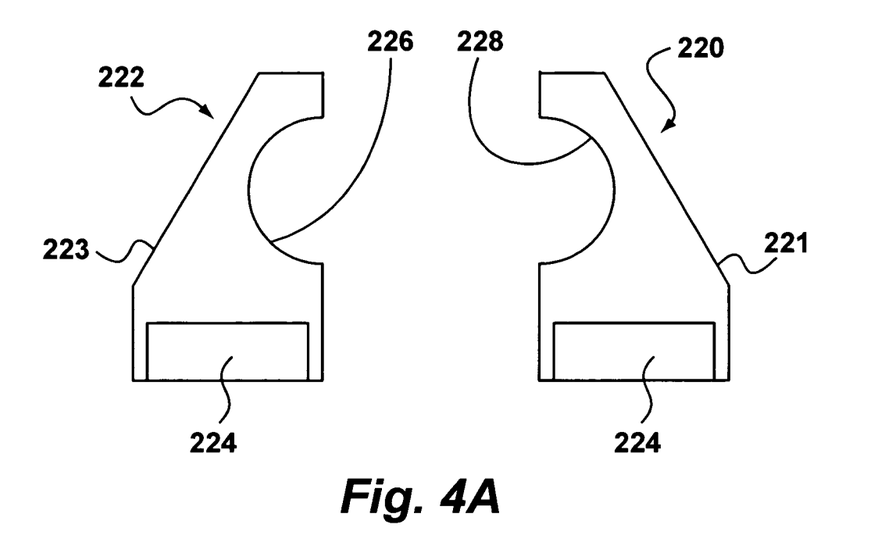
FIG. 4A is a front elevation view of one embodiment of folding guides in the transport configuration.
Figure 4B:
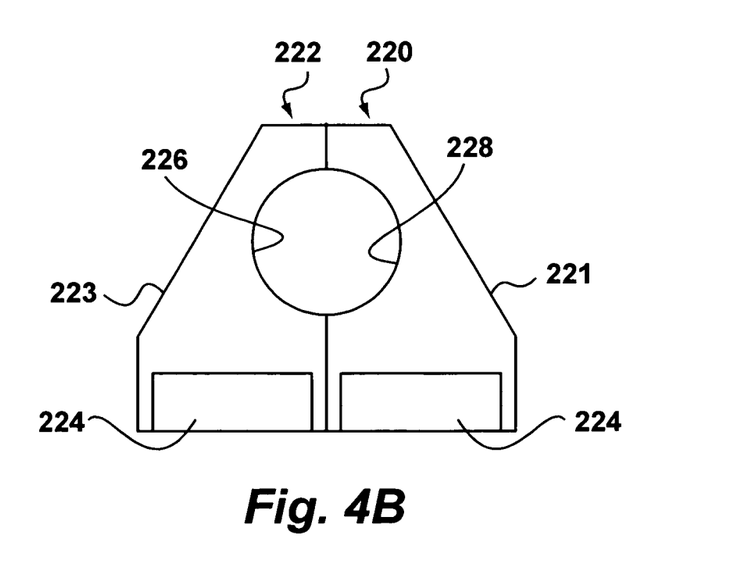
FIG. 4B is a front elevation view of one embodiment of folding guides in the injection configuration, after they have been moved to fold a device.

FIG. 4A illustrates lens folding guides 220 and 222. Right folding guide 220 has shoulder 221 and semi-cylindrical concave inner face 228. Left folding guide 222 may be a mirror image of right folding guide 220, with the former having shoulder 223 and semi-cylindrical concave face 226. Lens folding guides 220 and 222 may have keys 224, which are used to keep the folding guides oriented correctly during transition from the shipping mode to the injection mode, as described below. FIG. 4B shows the folding guides 220 and 220 in the injection mode, with the folding guides moved together. By forcing folding guides 220 and 222 together, respective concave faces 228 and 226 may force a lens to deform into a round cylinder, much like rolling one's tongue. In any case, a lens is deformed into a cylinder that is small enough to be inserted through an incision in an eye. If needed, friction-reducing additives may be used on surfaces to reduce friction as a lens or other device is deformed for insertion or is displaced from the folding guides.

Figure 5:
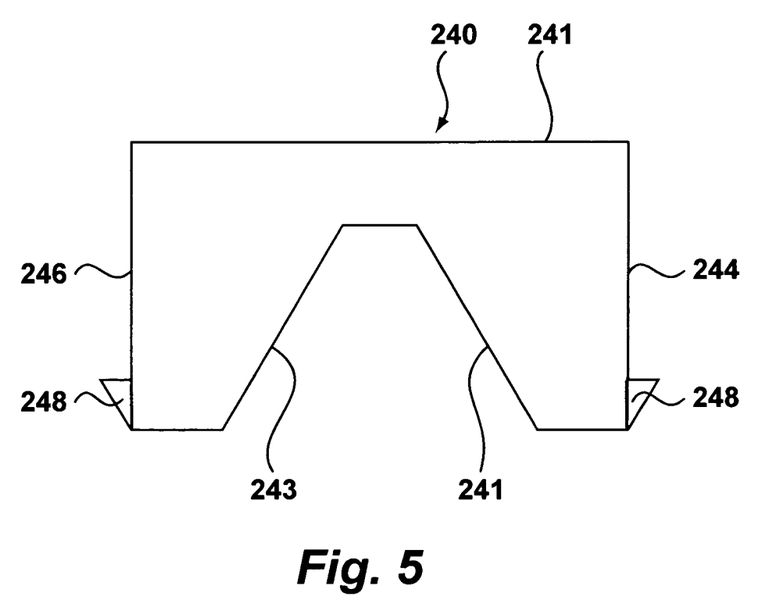
FIG. 5 is a front elevation view of the driving element of one embodiment of the invention.

FIG. 5 shows driving cam 240. Driving cam 240 has internal shoulders 241 and 243 that may be constructed and arranged to fit slideably against shoulders 221 and 223 of folding guides 220 and 222 (FIG. 4A). Driving cam 240 may have sides 244 and 246 that fit within a body, and two or more detent tabs 248.

Figure 6A:
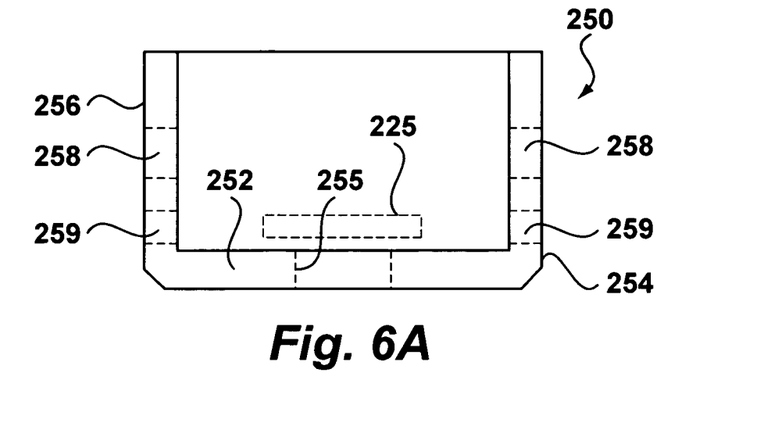
FIG. 6A is a front elevation view of the body of one embodiment of the invention.
Figure 6B:
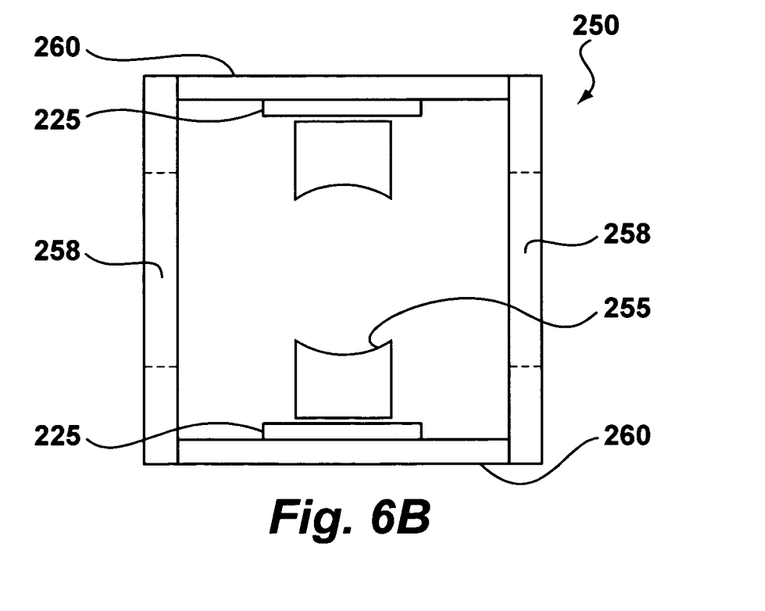
FIG. 6B is a plan view of the body of one embodiment of the invention with lens holder.

FIG. 6A is a front elevation view of "U" shaped body 250. Body 250 has a bottom 252 and sides 254 and 256 that mate with the sides 244 and 246, respectively, of driving cam 240 (FIG. 5). Each side 254 and 256 is fitted with a openings 258 and 259 into which the detents 248 of driving cam 240 fit. Body 250 has openings 255 within bottom 252 (FIG. 6B). Openings 255 are constructed and arranged to accommodate legs 234 and 236 of lens holder 230. Lens holder 230 may have any shape adapted to hold a foldable medical device. Front and back members 260 of body 250 may have attached thereto track guides 225, which may be disposed to allow key 224 (FIG. 4) to slide between track guide 225 and bottom 252 of body 250 as lens guides (FIG. 4) move to deform an implantable device before it is displaced from body 250. Although folding guides 220 and 222 are illustrated to form a cylindrical-shaped medical device after folding, it should be understood that other cross-sectional shapes may be formed, such as elliptical or rectangular.

Figure 7A:
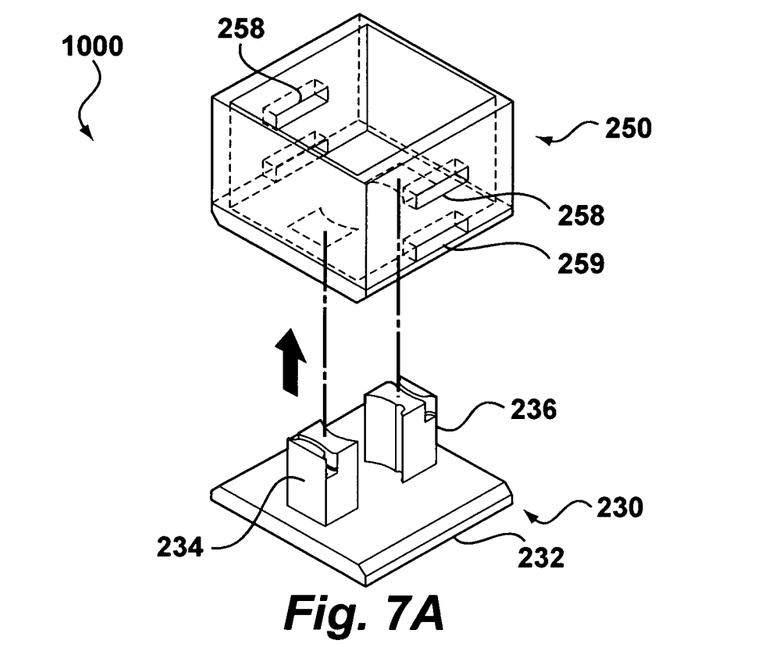
FIG. 7A is a perspective view showing placement of the lens holder in the bottom of the body to assemble the apparatus of the invention.

FIGS. 7A, 7B, 7C, 7D, 7E and 7F illustrate by isometric views the assembly and use of lens shipping, storage and injection system 1000. Referring to FIG. 7A, within injection system assembly 1000, body 250 is equipped with two rectangular upper shipping mode openings 258 and two rectangular lower injection mode openings 259. Each of openings 258 and 259 can be made of any convenient shape, but are intended to be constructed and arranged to accommodate tab 248 of driving cam 240 (FIG. 5), with one tab 248 within one hole 258 when assembly 1000 is in the shipping mode, and one tab 248 each within one hole 259 when assembly 1000 is in the injection mode. The shape of tab 248 is constructed and arranged to fit within either of the holes 258 and 259 so that the driving cam 240 can be moved from the shipping mode to the injection mode by deformation of either or both of driving cam 240 or sides 254 and 256 of body 250. While assembly 1000 may be disposable, alternate embodiments may be designed for reloading and reuse.

Figure 7B:
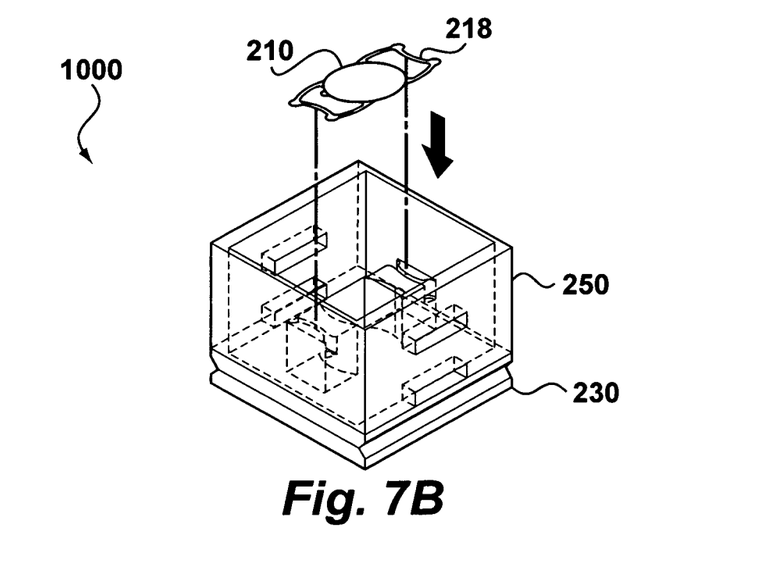
FIG. 7B is a perspective view showing placement of a lens in the lens holder.
Figure 7C:
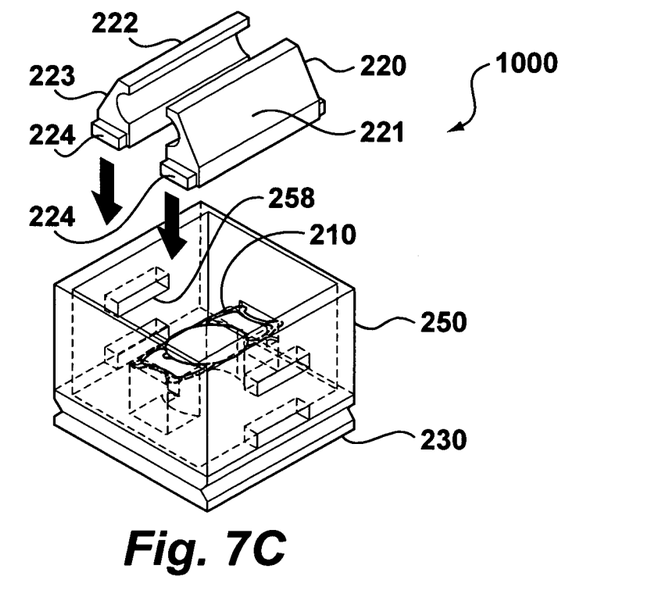
FIG. 7C is a perspective view showing placement of folding guides around the lens holder to assemble the apparatus of the invention.
Figure 7D:
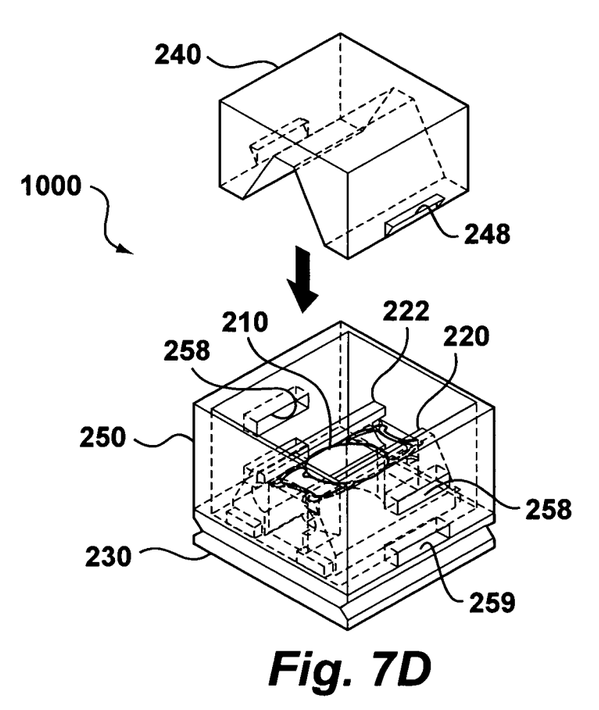
FIG. 7D is a perspective view showing placement of a driving element over the folding guides to assemble the apparatus of the invention.

Referring again to FIG. 7A, lens holder 230 may be inserted into body 250 through separate holes in bottom 230. Other shapes of lens holder 230 may be used. As illustrated in FIG. 7B, optic 210 and haptics 218 may then be placed on lens holder 230. Folding guides 220 and 222 may be placed within body 250, as illustrated in FIG. 7C. Then, driving cam 240 may be inserted into body 250, as illustrated in FIG. 7D until tabs 248 engage in the retaining slots 258, at which point system 1000 is in the shipping mode. The system may then be placed in a sealed container, which may contain a liquid suitable for storing and shipping the lens.

Figure 7E:
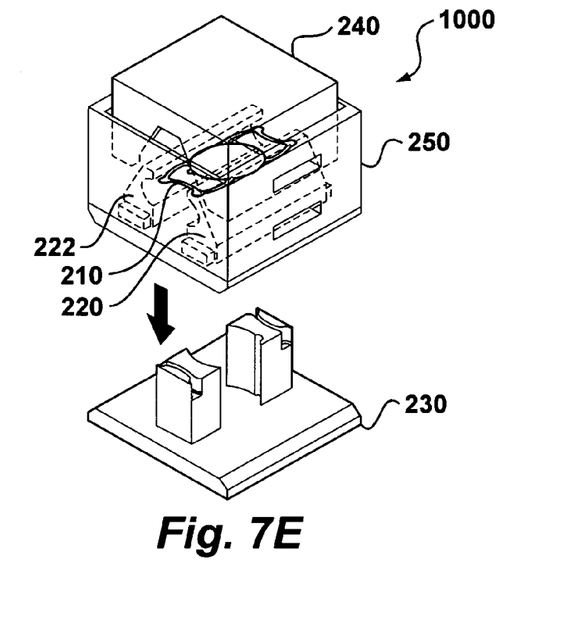
FIG. 7E is a perspective view of the apparatus showing removal of the lens holder.
Figure 7F:
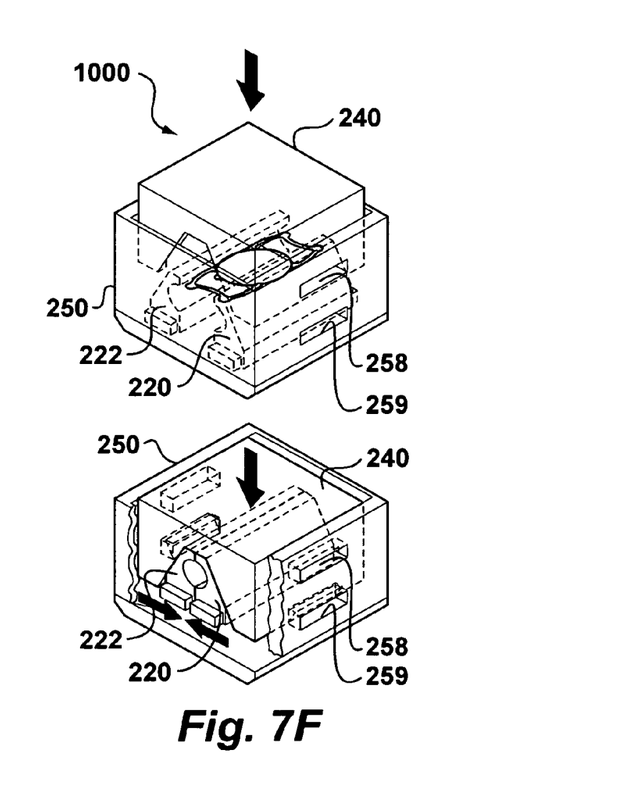
FIG. 7F is a perspective view of the apparatus showing closure of the folding guides.

Upon receipt of system 1000 by the user, the system 1000 must be transitioned from the shipping mode to the injection mode. To make the transition, the user simply removes lens holder 230 by detaching it from the bottom of the body 250, as illustrated in FIG. 7E. Once lens holder 230 is detached, the lens is suspended within body 250 between folding guides 220 and 222. The user then may depress driving cam 240 downward until tabs 248 are engaged with lower slots 259, as illustrated in FIG. 7F. In the process of depressing driving 240, folding guides 222 and 222 are pushed together as illustrated in the lower half of FIG. 7F. The inner concave shape of folding guides 220 and 222, within which sits optic 210, forces lens 210 to fold into a round shape that is suitable for injecting.

Figure 8A:
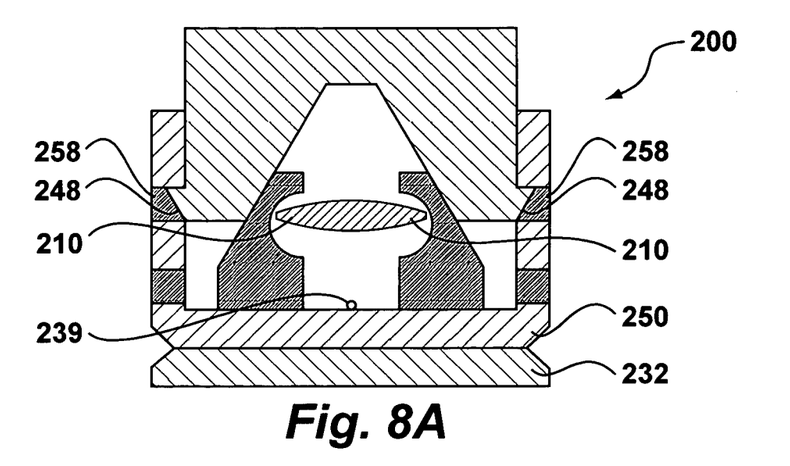
FIG. 8A is a center cross-section of the assembly of one embodiment of the invention in a shipping configuration.
Figure 8B:
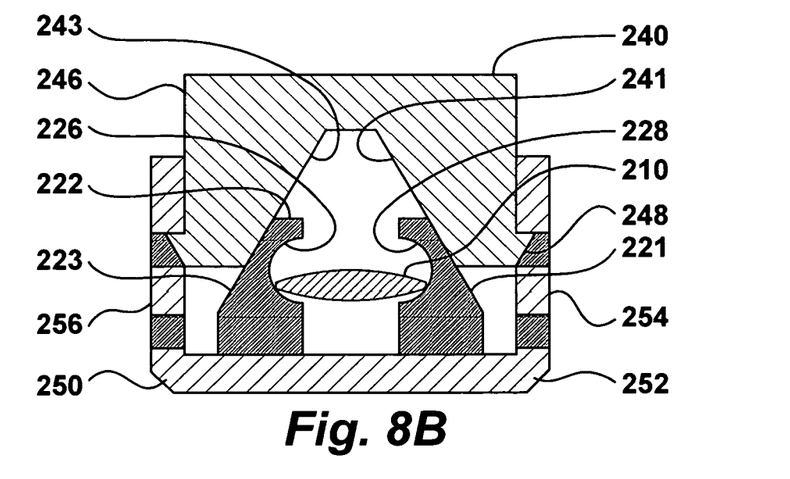
FIG. 8B is a center cross-section of the assembly of one embodiment of the invention after removal of the lens (or other device) holder.
Figure 8C:
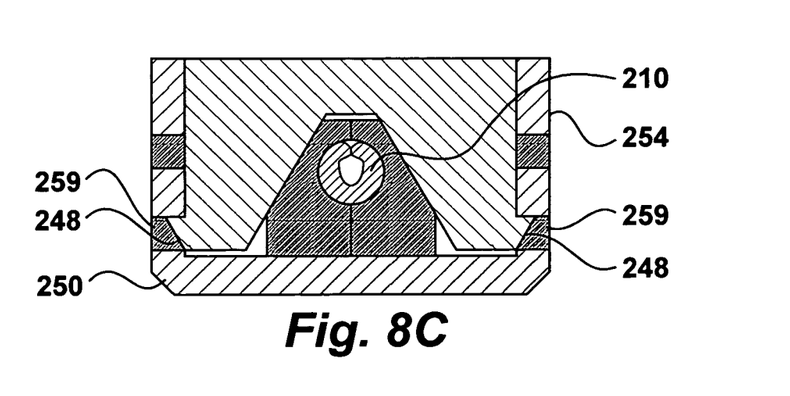
FIG. 8C is a center cross-section of the assembly of one embodiment of the invention after movement of the driving element to fold a lens.

FIGS. 8A, 8B and 8C show cross-sections halfway between front and back of the assembled device of system 1000. When assembly 1000 is received by the user, the first step in the preparation process is to remove lens holder 230 from body 250. To do so, the user grasps base 232 of lens holder 230 and pulls lens holder 230 away from the bottom of body 250 so that the legs 234 and 236 of the lens nest 230 are withdrawn through 250. During the removal step, lens 210, unable to slip out between the folding guides 220 and 222, is detached from lens holder 230 and comes to rest within the concave faces 226 and 228 of folding guides 222 and 220, respectively.

Referring to FIG. 8A, base 232 of lens holder 230 is shown at the bottom adjacent to the underside of the body 250. Locking nub 239 may be used to hold lens holder 230 in position within body 250. Detents 248 of driving cam 240 are locked within upper openings 258 of body 250 to secure driving cam 240 in the shipping mode. In FIG. 8B, lens holder 230 has been removed, as shown in FIG. 7E. Shoulder 223 of folding guide 222 is mated to the shoulder 243 of the driving cam 240.

Once lens holder 230 has been removed, the user may press down on the top of driving cam 240 until detents 248 move from upper holes 258 to lower holes 259. FIG. 8C shows the apparatus in the injection mode, after the user has moved the detents to the lower holes and the folding guides together. As lens 210 and haptics 212 are now contained within the concave faces 226 and 228, lens 210 and haptics 212 are rolled into the injection position as folding guides 220 and 222 are brought together. Once in the injection mode, an injection device, such as a syringe, can be attached to assembly 200 at one end, and an injection needle can be attached to the opposite end so that when the plunger of the syringe is operated, the lens is forced into the needle and then into a patient's eye, as shown in FIG. 9.

Figure 9:
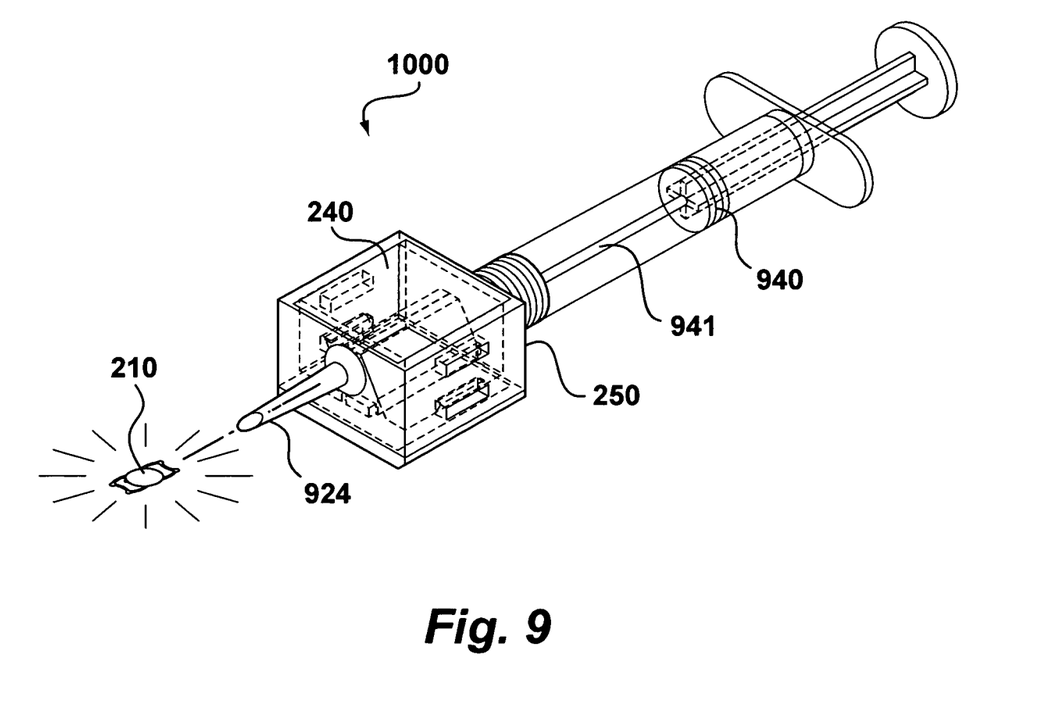
FIG. 9 is a perspective view of an assembly for insertion of a lens into an eye.

Referring to FIG. 9, needle 924 may be attached to one end of body 250 and a syringe, such as the stylus type syringe 940, may be attached to the opposite side of body 250. Syringe 940 may be collinear with folding guides 220 and 222 such that when the plunger of syringe 940 is pressed, a gelled fluid or, alternatively, a silicone-tipped push rod 941 in syringe 940 forces optic 210 into needle 924 for injection into a patient's eye.

In another embodiment, only one folding guide may be used. For instance, the concave inner face that was opposing one folding guide, such as guide 222 of FIG. 10C, can be part of body 250. Consequently, only one movable folding guide (220) would be needed. Driving cam 240 can be modified appropriately to move only one folding guide.

The material or materials for the components of system 1000 are preferably capable of withstanding high temperatures, such as those encountered in an autoclave. Moreover, the material for the shipping container should be such that it does not leach into the solution surrounding the lens, lest the lens be contaminated by the container material. Possible materials include polyolefins, nylon, Teflon and other plastics.

In another embodiment, a slipping agent (a material to reduce friction between surfaces) may be applied to one or more of the components of system 1000 to aid in the transition and/or injection processes. Such slipping agent may be any of or a combination of known slipping agents.

The body 250 of the system 1000 may contain a solution, such as saline, that provides a suitable environment for a medical implant (e.g., a lens). Body 250 may be sealable for shipping, or, instead, body 250 in the shipping mode may be placed within a sealable container for transport to the user. During shipment, system 1000 may or may not have the injection mechanism 924 or the injection actuation mechanism 940 attached to body 250.

The present invention has been described in terms of specific exemplary embodiments. In accordance with the present invention, the parameters for a system may be varied, typically with a design engineer specifying and selecting them for the desired application. Further, it is contemplated that other embodiments, which may be devised readily by persons of ordinary skill in the art based on the teachings set forth herein, may be within the scope of the invention, which is defined by the appended claims. The present invention may be modified and practiced in different but equivalent manners that will be apparent to those skilled in the art and having the benefit of the teachings set forth herein.

What is claimed is:

1. Apparatus for transporting and injecting a foldable medical device through an opening, comprising:
    a body;
    a holder for the foldable medical device, the holder being adapted to be placed within the body and having a rigid base and legs;
    said legs extending upward from the base and adapted to support the medical device within the body
    a rigid folding guide adapted to move within the body in a first direction for folding the medical device when the folding guide is moved toward the medical device;
    a driving cam movable in a second direction different from the first direction for moving the folding guide in the first direction when the driving cam is moved from a first position to a second position;
    an insertion device to displace the medical device from the folding guide and through the opening when the folding guide has been moved to fold the medical device and
    said legs being movable from a first position blocking movement of said rigid folding guide in said first direction to a second position allowing movement of said rigid folding guide in said first direction.

2. The apparatus of claim 1 wherein the foldable medical device is an intraocular lens and the opening is an incision into an eye.

3. The apparatus of claim 1 including a second folding guide movable within the body, each folding guide comprising a semi-cylindrical concave surface adapted to surround the foldable medical device and fold the device as the surfaces move toward the device so as to form a cylinder.

4. The apparatus of claim 3 wherein the driving cam comprises two sloping surfaces that engage a sloping surface on the rigid folding guides to move the folding guides so as to fold the medical device when the driving cam is moved in a selected direction.

5. The apparatus of claim 1 wherein the driving cam comprises a sloping surface and is adapted to cooperate with a sloping surface on the folding guide to move the folding guide so as to fold the medical device when the driving cam is moved in the first direction.

6. The apparatus of claim 1 wherein the insertion device to displace the medical device comprises a syringe containing a liquid that is operated to drive the folded medical device.

7. The apparatus of claim 1 wherein the insertion device to displace the medical device comprises a mechanical plunger.

8. The apparatus of claim 1 wherein the body contains a track guide and the folding guide further comprises a key, the key being adapted to move within the track guide when the folding guide moves within the body.

9. The apparatus of claim 1 wherein a selected surface of the apparatus further comprises a friction-reducing agent.

10. Apparatus as claimed in claim 1 wherein the body includes at least one first retaining slot and said driving cam includes at least one detent tab extending into the retaining slot to prevent movement of the driving cam with respect to the body.

11. Apparatus as claimed in claim 10 further including at least one additional retaining slot located below the first retaining slot in the body and at least one addition detent tab on the driving cam to lock the driving cam in a second position after the driving cam is moved from a first position to a second position.

12. Apparatus for transporting and injecting a foldable medical device through an opening, comprising:
    a body;
    a holder for the foldable medical device, the holder positioned within the body and having a rigid base and legs;
    said legs extending upwardly from said base and having a channel supporting the medical device;
    a rigid folding guide adapted to move within the body in a first direction for folding the medical device when the folding guide is moved toward the medical device; and
    a driving cam movable in a second direction different from the first direction for moving the folding guide in said first direction when the driving cam is moved from a first position to a second position wherein said legs are movable from a first position which blocks the movement of said rigid folding guide in said first direction to a second position which allows movement of said rigid folding guide in said first direction.

13. The apparatus of claim 12 wherein the folding guide includes two folding guide members each movable within the body and each comprising a semi-cylindrical concave surface adapted to surround the foldable medical device and fold the device as the surfaces move toward the device so as to form a cylinder.

14. Apparatus for transporting and injecting a foldable medical device through an opening, comprising:
 a body;
 a holder for the foldable medical device, the holder being adapted to be placed within the body and having a rigid base and legs for supporting the medical device;
 a rigid folding guide adapted to move in a first direction within the body for folding the medical device when the folding guide is moved toward the medical device; and
 a driving cam adapted to move in a second direction different from the first direction for moving the folding guide in said first direction when the driving cam is moved from a first position to a second position
 wherein said legs are moveable from a first position which blocks movement of said rigid folding guide in said first direction to a second position which allows movement of said rigid folding guide in said first direction.

15. Apparatus as claimed in claim 14 wherein the means for supporting the medical device comprises a pair of upstanding legs having channels at a top portion of the legs.

16. Apparatus as claimed in claim 14 wherein the driving cam has a sloping surface that engages a sloping surface on the rigid folding guide.

17. Apparatus as claimed in claim 14 including a second folding guide movable within the body, said folding guides each having a sloping surface, said driving cam having two opposing sloping surfaces adapted to contact the sloping surfaces of the folding guides to thereby move the folding guides toward each other when the driving cam is moved.

\* \* \* \* \*